United States Patent
Miyazaki et al.

(10) Patent No.: US 6,380,427 B1
(45) Date of Patent: Apr. 30, 2002

(54) PROCESS FOR PURIFICATION OF (METH)ACRYLIC ACID

(75) Inventors: Seiji Miyazaki; Akira Ogawa; Yasutaka Nakashima; Yoshiaki Kobayashi; Mikiyoshi Araki, all of Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/463,664

(22) PCT Filed: Jul. 29, 1998

(86) PCT No.: PCT/JP98/03380

§ 371 Date: Jan. 28, 2000

§ 102(e) Date: Jan. 28, 2000

(87) PCT Pub. No.: WO99/06348

PCT Pub. Date: Feb. 11, 1999

(30) Foreign Application Priority Data

Jul. 30, 1997 (JP) .............................. 9-204738

(51) Int. Cl.[7] .............................................. C07C 51/42
(52) U.S. Cl. ...................... 562/600; 560/205; 562/599; 562/606
(58) Field of Search .................. 560/205; 562/599, 562/600, 606

(56) References Cited

U.S. PATENT DOCUMENTS

| | | | |
|---|---|---|---|
| 3,882,167 A | * | 5/1975 | Lohmar et al. ............. 560/205 |
| 3,962,074 A | * | 6/1976 | Schropp ..................... 210/634 |
| 4,113,574 A | | 9/1978 | Schumacher et al. |
| 4,493,719 A | * | 1/1985 | Wintermantel et al. ....... 62/532 |
| 4,780,568 A | * | 10/1988 | Pascoe ....................... 562/599 |
| 5,386,052 A | * | 1/1995 | Sakakura .................... 560/205 |
| 5,504,247 A | * | 4/1996 | Saxer et al. ................ 562/600 |
| 5,606,102 A | * | 2/1997 | Fauconet et al. ........... 560/205 |

FOREIGN PATENT DOCUMENTS

| | | | |
|---|---|---|---|
| EP | 0023774 | * | 2/1981 |
| EP | 784 046 | | 7/1997 |
| GB | 1235208 | * | 6/1971 |
| JP | 45-32417 | | 10/1970 |
| JP | 46-10535 | | 3/1971 |
| JP | 47-31924 | | 11/1972 |
| JP | 49-45020 | | 4/1974 |
| JP | 49-88819 | | 8/1974 |
| JP | 54-66617 | | 5/1979 |
| JP | 56-16438 | | 2/1981 |
| JP | 58-118540 | | 7/1983 |
| JP | 60-178842 | | 9/1985 |
| JP | 61-50937 | | 3/1986 |
| JP | 64-9956 | | 1/1989 |
| JP | 64-40441 | | 2/1989 |
| JP | 1-226845 | | 9/1989 |
| JP | 1-242547 | | 9/1989 |
| JP | 5-331097 | | 12/1993 |
| JP | 5-331098 | | 12/1993 |
| JP | 6-329580 | | 11/1994 |
| JP | 7-48311 | | 2/1995 |
| JP | 7-82210 | | 3/1995 |
| JP | 7-89915 | | 4/1995 |
| JP | 9-157212 | | 6/1997 |
| JP | 9-183752 | | 7/1997 |
| JP | 9-183753 | | 7/1997 |
| JP | 9-202747 | | 8/1997 |
| JP | 9-227445 | | 9/1997 |
| JP | 409227445 | * | 9/1997 |
| RU | 639858 | | 12/1978 |

* cited by examiner

*Primary Examiner*—Paul J. Killos
*Assistant Examiner*—Taylor V. Oh
(74) *Attorney, Agent, or Firm*—Oblon, Spivak, McClelland, Maier & Neustadt, P.C.

(57) ABSTRACT

A process for purification of (meth)acrylic acid which comprises adding to a crude (meth)acrylic acid one or two or more polar organic substances as a second component at a concentration of 1–35% by weight, crystallizing (meth)acrylic acid from the resulting (meth)acrylic acid solution, and separating the precipitated crystal of (meth)acrylic acid and a mother liquor from each other.

10 Claims, No Drawings

PROCESS FOR PURIFICATION OF (METH)ACRYLIC ACID

TECHNICAL FIELD

The present invention relates to a process for the purification of (meth)acrylic acid, and particularly to a process for the purification of (meth)acrylic acid by crystallization with addition of a second component to a crude (meth)acrylic acid.

Hereupon, the term "(meth)acrylic acid" means acrylic acid or methacrylic acid.

BACKGROUND ART

A product obtained by subjecting isobutylene, tert-butyl alcohol, methacrolein or isobutyl aldehyde to one or two stage catalytic gas phase oxidation with molecular oxygen contains carboxylic acids such as formic acid, acetic acid, propionic acid, maleic acid, citraconic acid, benzoic acid, toluic acid and terephthalic acid or aldehydes such as formaldehyde, acetaldehyde, propionaldehyde, methacrolein, benzaldehyde, tolualdehyde and furfural as by-products in addition to the objective methacrylic acid (boiling point 161° C./760 mmHg, melting point 15° C.). Most of these impurities can be separated by usual purification means such as extraction and distillation. However, it is very difficult to remove impurities contained in a slight amount, such as maleic acid, citraconic acid and aldehydes. Especially, aldehydes have absorption in ultraviolet region, and, therefore, methacrylic acid products in which aldehydes remain in a large amount suffer from the problem of coloration. In order to avoid the problem of coloration, residual amount of aldehydes must be reduced as much as possible. Such problems due to impurities occur not only in the production of methacrylic acid, but also in the production of acrylic acid by subjecting propylene and acrolein to gas phase oxidation.

Furthermore, in purification by distillation, since the distillation temperature is as high as about 80° C. even if it is controlled as low as possible, (meth)acrylic acid and others undergo polymerization reaction in a distillation column to often cause troubles such as clogging of the distillation column. Therefore, a distillation operation is generally carried out with addition of polymerization inhibitor, but there is the possibility of incorporation of the polymerization inhibitor into the products. For this reason, the polymerization inhibitor cannot be added in such a large amount as capable of completely avoiding the troubles caused by polymerization reaction. Thus, at present, such troubles due to the polymerization reaction cannot be avoided.

Under the circumstances, attempts have been made to remove impurities in (meth)acrylic acid by crystallization method which causes substantially no troubles due to polymerization reaction. For example, JP-A-7-163802 discloses crystallization method and apparatus; JP-B-45-32417 discloses a method for purifying methacrylic acid containing a large amount of non-polar organic solvents such as butadiene, heptane and toluene by crystallization method; JP-A-7-82210 discloses a method for adiabatic cooling by evaporating added water; and JP-A-9-157212 discloses a method for adiabatic cooling by evaporating added liquefied propylene or liquefied isobutene.

However, in the crystallization method of JP-A-7-163802, the crystallization apparatus usable therefor is restricted, and the method cannot be applied to other general crystallization apparatuses. In the method of JP-B-45-32417, a large amount such as 40–85% of non-polar organic solvent must be present as a second component in methacrylic acid, which results in decrease of methacrylic acid concentration in the treated solution. For efficient recovery of methacrylic acid from the solution, the temperature of the solution at the time of crystallization must be decreased to a very low temperature of –20° C.—–80° C. As a result, there are problems that the crystallization apparatuses must be large in scale and a great energy is required for cooling. The methods of JP-A-7-82210 and JP-A-9-157212 are limited to particular cooling methods such as adiabatic cooling, so cannot apply to general crystallization apparatus.

An object of the present invention is to provide a process for the purification of (meth)acrylic acid by crystallization method according to which impurities which are contained in (meth)acrylic acid and are difficult to diminish by distillation can be removed by an economical method which does not use a large amount of a second component and does not require very low temperatures.

Another object of the present invention is to provide an economical process for producing (meth)acrylic acid esters by using a mother liquor separated in crystallization, as it is, as a starting material for (meth)acrylic acid esters.

DISCLOSURE OF THE INVENTION

The present invention is a process for the purification of (meth)acrylic acid which comprises adding to a crude (meth)acrylic acid one or two or more polar organic substances at a concentration of 1–35% by weight as a second component, crystallizing (meth)acrylic acid from the (meth)acrylic acid solution, and separating the precipitated crystal of (meth)acrylic acid and the mother liquor from each other.

BEST MODE FOR CARRYING OUT THE INVENTION

The crude (meth)acrylic acid to be subjected to purification in the present invention means a crude methacrylic acid or a crude acrylic acid. The crude methacrylic acid can be produced by various methods such as direct oxidation method and ACH method. As the method for producing the crude methacrylic acid, there are, for example, a method which comprises subjecting a compound selected from the group consisting of isobutylene, tert-butyl alcohol, methacrolein and isobutyl aldehyde to a direct oxidation comprising catalytic gas phase oxidation in one- or two-stages with molecular oxygen to obtain a reaction gas, condensing the reaction gas to obtain a condensed liquid, or adding water to the condensed liquid of the reaction gas or absorbing the reaction gas in water to obtain an aqueous methacrylic acid solution, extracting methacrylic acid from the condensed liquid or the aqueous methacrylic acid solution using an organic solvent, and removing the organic solvent and nonvolatile matters by distillation to obtain a crude methacrylic acid and a method which comprises separating methacrylic acid by-produced in ACH method by extraction or distillation to obtain a crude methacrylic acid. Furthermore, the crude acrylic acid can be obtained in the similar manner to the production of the crude methacrylic acid by the one- or two-stage catalytic gas phase oxidation of, for example, propylene and/or acrolein with molecular oxygen.

The crude (meth)acrylic acid hereupon is (meth)acrylic acid containing the impurities to be removed by the purification process of the present invention. Even the (meth)acrylic acid purified by precision distillation or crystallization is regarded to be the crude (meth)acrylic acid to be purified in the present invention if it contains the impurities to be removed by the process of the present invention.

In the process of the present invention, first, one or two or more polar organic substances are added to the crude (meth)acrylic acid so as to give a concentration of 1–35% by weight as a second component.

The second component is not limited as far as they are polar organic substances that do not form a solid solution with (meth)acrylic acid at crystallization. As such second components, mention may be made of, for example, methanol, ethanol, propanol, butanol, diethyl ether, dioxane, tetrahydrofuran, acetone, methyl ethyl ketone, methyl isobutyl ketone, methyl formate, ethyl formate, methyl acetate, ethyl acetate, methyl methacrylate, ethyl methacrylate, methyl acrylate, and ethyl acrylate. The second component is preferably selected from the group consisting of methanol, methyl methacrylate and methyl acrylate. These substances may be used each alone or in admixture of two or more as the second component.

The second component is added in such an amount as to give a concentration of 1–35% by weight, preferably 3–30% by weight. If the concentration of the second component is less than 1% by weight, since the difference between the temperature at which crystal of (meth)acrylic acid begins to be precipitated, namely, the crystal precipitation temperature and the freezing point of (meth)acrylic acid is very small, crystallizing operation becomes difficult and, in some cases, the crystallizing operation per se becomes impossible because the crude (meth)acrylic acid completely solidifies. On the other hand, if the concentration of the second component added is more than 35% by weight, the crystal precipitation temperature sharply lowers and, hence, a large energy and a high cost are required for cooling.

From the point of operation at crystallization, kind and amount of the second component are preferably selected so that the crystal precipitation temperature of the crude (meth)acrylic acid after the addition of the second component falls within the range of −10° C.–−10° C.

Then, crystallization of the crude (meth)acrylic acid to which the second component has been added is carried out in a crystallizing vessel. The operation temperature of crystallization may be not higher than the crystal precipitation temperature. From the point of operability, the operation temperature is preferably −10° C.–−10° C.

For the crystallization, known apparatus can be used, such as those described in "Kagaku Kogaku Binran (Handbook of Chemical Engineering)", the fifth revision (1988). The type of the operation of crystallization may be either batch process or continuous process.

Then, the thus obtained crystal of (meth)acrylic acid and the mother liquor are separated from each other. Crystal of (meth)acrylic acid can be obtained by such crystallizing method. On the other hand, the separated mother liquor usually contains the second component added, concentrated impurities and (meth)acrylic acid.

For the separation of the crystal from the mother liquor, any methods which can separate solid and liquid from each other can be employed, and there is no limitation. For example, known methods such as filtration method and centrifugation method can be utilized. As a specific example of the apparatus for the separation, mention may be made of KCP apparatus described in Chuzo Shimizu, "Purification of Organic Compounds by KUREHA Continuous Crystal Purification Apparatus" in "Chemical Engineering", Vol. 27, No. 3 (1982), p. 49. The type of the separation may be either batch process or continuous process.

From the separated mother liquor, (meth)acrylic acid and the second component can be recovered and reused or re-purified. The (meth)acrylic acid recovered from the mother liquor can also be used as a starting material for the preparation of (meth)acrylic acid esters by esterification. Since the separated mother liquor can be used, as it is, as a starting material for the preparation of (meth)acrylic acid esters, it is preferred from the economical view point to use the mother liquor without subjecting to re-purification. In preparation of esters using the separated mother liquor, an alcohol and/or (meth)acrylic acid, which are starting materials, may further be added to the mother liquor.

When the mother liquor separated is used as a starting material for (meth)acrylic acid esters, the second component used can be any of the substances satisfying the above conditions as in the case of the crystallization, but preferred are those which hardly inhibit or hinder the esterification reaction which gives (meth)acrylic acid esters. That is, preferred are those which hardly react with (meth)acrylic acid, a (meth)acrylic acid ester which is the desired product, an alcohol as a starting material for the (meth)acrylic acid ester and water under acidic conditions, and/or one of a (meth)acrylic acid ester which is the desired product and an alcohol as a starting material for the (meth)acrylic acid ester. Examples of these second components are methanol, ethanol, propanol, butanol, diethyl ether, tetrahydrofuran, methyl methacrylate, ethyl methacrylate, methyl acrylate, and ethyl acrylate. Especially preferred are a (meth)acrylic acid ester which is the desired product and/or an alcohol which is a starting material for the (meth)acrylic acid ester, from the viewpoint of less superfluous matter mixed in the reaction system.

When the thus separated mother liquor is used as a starting material for a (meth)acrylic acid ester, the second component is added to the crude (meth)acrylic acid in such an amount as to give a concentration of 1–35% by weight, preferably 3–30% by weight, in the same manner as in the case of the crystallization alone.

As an example of application of this process, mention may be made of a process which comprises adding methanol and/or methyl (meth)acrylate as a second component to a crude (meth)acrylic acid, subjecting the mixture to crystallization, separating the crystal of (meth)acrylic acid and the mother liquor from each other, and using the (meth)acrylic acid in the separated mother liquor as a starting material for methyl (meth)acrylate. This process is much superior in that purified (meth)acrylic acid and methyl (meth)acrylate can be produced with substantially no loss of (meth)acrylic acid. In this case, impurities concentrated by crystallization are introduced into the step of the production of methyl (meth)acrylate. However, there occur no special problems because in the case of, for example, methacrylic acid, those impurities which can hardly be separated from methacrylic acid (boiling point 161° C./760 mmHg) by distillation can be easily separated from methyl methacrylate (boiling point 100.8° C./760 mmHg) by distillation. This is the same in the production of methyl acrylate.

The present invention will be explained in more detail by the following Examples and Comparative Examples. These Examples and Comparative Examples never limit the scope of the invention.

The crude methacrylic acid used in the Examples and Comparative Examples was obtained by subjecting methacrolein to catalytic gas phase oxidation with molecular oxygen, then condensing the resulting reaction gas and extracting methacrylic acid, unless otherwise notified.

Furthermore, as cooling media used in the crystallization, water and/or ice were used in a cold water bath and aqueous ethylene glycol solution was used in a cooling media bath, unless otherwise notified.

EXAMPLE 1

A mixed solution of 950 g of a crude methacrylic acid containing the impurity shown in Table 1 and 50 g of methanol (a second component) was charged in a 1 liter glass beaker and cooled to 7° C. by a cold water bath with stirring. In this case, the crystal precipitation temperature was 9° C. After cooling, the precipitated crystal was separated by filtration to obtain 280 g of crystalline purified methacrylic acid containing the impurity shown in Table 1.

TABLE 1

| Impurities | Crude methacrylic acid (wt %) | Purified methacrylic acid (wt %) |
|---|---|---|
| Acetic acid | 0.0042 | 0.0008 |
| Propionic acid | 0.0239 | 0.0038 |
| Maleic acid | 0.1504 | 0.0010 |
| Citraconic acid | 0.0373 | 0.0086 |
| Tolualdehyde | 0.0338 | 0.0063 |

COMPARATIVE EXAMPLE 1

The same procedure as in Example 1 was carried out without adding the second component. That is, 1000 g of the crude methacrylic acid containing the impurity shown in Table 1 was charged in a 1 liter glass beaker and cooled to 10° C. by a cold water bath with stirring. In this case, the crystal precipitation temperature was 14.5° C. After cooling, the solution in the glass beaker completely solidified, and the impurities and purified methacrylic acid could not be taken out.

COMPARATIVE EXAMPLE 2

A mixed solution of 600 g of a crude methacrylic acid containing the impurity shown in Table 2 and 400 g of methanol was charged in a 1 liter glass beaker and cooled to −10° C. by a cooling media bath with stirring. In this case, even when the solution temperature reached −10° C., no crystal was precipitated, and the impurities and purified methacrylic acid could not be taken out.

Therefore, the same procedure as above was carried out using a dry ice-methanol bath as the cooling media bath. That is, a mixed solution of 600 g of the crude methacrylic acid containing the impurity shown in Table 2 and 400 g of methanol was charged in a 1 liter glass beaker and cooled to −30° C. by a dry ice-methanol bath with stirring. In this case, the crystal precipitation temperature was −23° C. After cooling, the precipitated crystal was separated by filtration to obtain 350 g of crystalline purified methacrylic acid containing the impurity shown in Table 2. However, this process requires cooling to a very low temperature of −30° C., and was very low in efficiency.

TABLE 2

| Impurities | Crude methacrylic acid (wt %) | Purified methacrylic acid (wt %) |
|---|---|---|
| Acetic acid | 0.0042 | 0.0025 |
| Propionic acid | 0.0239 | 0.0102 |
| Maleic acid | 0.1504 | 0.0010 |
| Citraconic acid | 0.0373 | 0.0188 |
| Tolualdehyde | 0.0338 | 0.0150 |

EXAMPLE 2

A mixed solution of 780 g of a crude methacrylic acid containing the impurity shown in Table 3 and 220 g of methyl methacrylate was charged in a 1 liter glass beaker and cooled to −7° C. by a cooling media bath with stirring. In this case, the crystal precipitation temperature was 0° C. After cooling, the precipitated crystal was separated by filtration to obtain 340 g of crystalline purified methacrylic acid containing the impurity shown in Table 3.

TABLE 3

| Impurities | Crude methacrylic acid (wt %) | Purified methacrylic acid (wt %) |
|---|---|---|
| Acetic acid | 0.0042 | 0.0023 |
| Propionic acid | 0.0239 | 0.0102 |
| Maleic acid | 0.1504 | 0.0010 |
| Citraconic acid | 0.0373 | 0.0182 |
| Tolualdehyde | 0.0338 | 0.0142 |

EXAMPLE 3

The same procedure as in Example 1 was carried out using, as the crude methacrylic acid, the crystalline methacrylic acid which was obtained in the process of Example 1 and was molten. That is, a mixed solution of 950 g of a crude methacrylic acid containing the impurity shown in Table 4 which was obtained by once carrying out the crystallization in the process of Example 1 and 50 g of methanol was charged in a 1 liter glass beaker and cooled to 7° C. by a cold water bath with stirring. In this case, the crystal precipitation temperature was 9° C. After cooling, the precipitated crystal was separated by filtration to obtain 320 g of crystalline purified methacrylic acid containing the impurity shown in Table 4.

TABLE 4

| Impurities | Crude methacrylic acid (wt %) | Purified methacrylic acid (wt %) |
|---|---|---|
| Acetic acid | 0.0008 | 0.0003 |
| Propionic acid | 0.0038 | 0.0007 |
| Maleic acid | 0.0010 | Undetected |
| Citraconic acid | 0.0086 | 0.0010 |
| Tolualdehyde | 0.0063 | 0.0012 |

EXAMPLE 4

The same procedure as in Example 2 was carried out using, as the crude methacrylic acid, the crystalline methacrylic acid which was obtained in the process of Example 2 and was molten. That is, a mixed solution of 780 g of a crude methacrylic acid containing the impurity shown in Table 5 which was obtained by once carrying out the crystallization in the process of Example 2 and 220 g of methyl methacrylate was charged in a 1 liter glass beaker and cooled to −6° C. by a cooling media bath with stirring. In this case, the crystal precipitation temperature was 0° C. After cooling, the precipitated crystal was separated by filtration to obtain 260 g of crystalline purified methacrylic acid containing the impurity shown in Table 5.

TABLE 5

| Impurities | Crude methacrylic acid (wt %) | Purified methacrylic acid (wt %) |
|---|---|---|
| Acetic acid | 0.0023 | 0.0013 |
| Propionic acid | 0.0102 | 0.0050 |
| Maleic acid | 0.0010 | (Undetected) |
| Citraconic acid | 0.0182 | 0.0084 |
| Tolualdehyde | 0.0142 | 0.0067 |

EXAMPLE 5

Fifty-four kilograms per hour of a crude methacrylic acid containing the impurity shown in Table 6 and 4 kg/h of methanol were introduced into a crystallizing vessel and cooled to 6° C. by a cooling media with stirring. The crystal precipitation temperature of the solution mixed at the above proportion was 10° C. After cooling the slurry containing the precipitated crystal was continuously charged in KCP apparatus (manufactured by Kureha Engineering Co., Ltd.) to obtain 13 kg/h of crystalline purified methacrylic acid containing the impurity shown in Table 6 and 45 kg/h of a methacrylic acid solution containing methanol.

TABLE 6

| Impurities | Crude methacrylic acid (wt %) | Purified methacrylic acid (wt %) | Methyl methacrylate (wt %) |
|---|---|---|---|
| Acetic acid | 0.0067 | 0.0001 | (Undetected) |
| Propionic acid | 0.0662 | 0.0013 | (Undetected) |
| Maleic acid | 0.2185 | (Undetected) | (Undetected) |
| Citraconic acid | 0.2135 | (Undetected) | (Undetected) |
| Tolualdehyde | 0.0735 | (Undetected) | (Undetected) |

Forty-five kilograms of the resulting methacrylic acid solution containing methanol was mixed with 6 kg of the crude methacrylic acid and 22 kg of methanol, followed by esterification of them and purification of the ester by distillation to prepare methyl methacrylate. As a result, 69 kg of methyl methacrylate containing the impurity shown in Table 6 was obtained.

EXAMPLE 6

Acrolein was subjected to catalytic gas phase oxidation with molecular oxygen, and then the resulting reaction gas was subjected to condensation and extraction. The extract was distilled to obtain a crude acrylic acid. The impurity contained in this crude acrylic acid is shown in Table 7.

Fifty kilograms per hour of this crude acrylic acid and 2 kg/h of methanol were introduced into a crystallizing vessel and cooled to 5° C. by a cooling media with stirring. The crystal precipitation temperature of the mixed solution of the above proportion was 8° C. After cooling the slurry containing the precipitated crystal was continuously introduced into KCP apparatus (manufactured by Kureha Engineering Co., Ltd.) to obtain 12 kg/h of crystalline purified acrylic acid containing the impurity shown in Table 7 and 40 kg/h of an acrylic acid solution containing methanol.

TABLE 7

| Impurities | Crude acrylic acid (wt %) | Purified acrylic acid (wt %) | Methyl acrylate (wt %) |
|---|---|---|---|
| Acetic acid | 1.4500 | 0.0029 | (Undetected) |
| Propionic acid | 0.2825 | (Undetected) | (Undetected) |
| Acrolenin | 0.0324 | (Undetected) | (Undetected) |
| Furfural | 0.0624 | 0.0001 | (Undetected) |

Thirty-nine kilograms of the resulting acrylic acid solution containing methanol was mixed with 6 kg of the crude acrylic acid and 12 kg of methanol, followed by esterification of them and purification of the ester by distillation to prepare methyl acrylate. As a result, 51 kg of methyl acrylate containing the impurity shown in Table 7 was obtained.

Industrial Applicability

According to the present invention, those impurities which are contained in (meth)acrylic acid and are difficult to diminish by distillation can be removed by an economical method which does not use a large amount of a second component and requires no very low temperature. Furthermore, by using a mother liquor separated in crystallization as a starting material for (meth)acrylic acid esters, (meth)acrylic acid esters can be produced with effective utilization of (meth)acrylic acid in the crude (meth)acrylic acid.

What is claimed is:

1. A process for purification of (meth)acrylic acid which comprises adding to a crude (meth)acrylic acid as a first component, at least one alcohol as a second component at a concentration of 1–35% by weight, crystallizing (meth)acrylic acid from the resulting (meth)acrylic acid solution, and separating precipitated crystals of (meth)acrylic acid from the crystallization mother liquor.

2. A process according to claim 1, wherein the second component is an alcohol which does not form a solid solution with (meth)acrylic acid at the time of the crystallization.

3. A process according to claim 2, wherein said alcohol is selected from the group consisting of methanol, ethanol, propanol, and butanol.

4. A process according to claim 3, wherein the second component is methanol.

5. A process according to claim 1, wherein the concentration of the second component is 3–30% by weight.

6. A process for producing a (meth)acrylic acid ester which comprises adding to a crude (meth)acrylic acid as a first component, at least one alcohol as a second component at a concentration of 1–35% by weight, crystallizing (meth) acrylic acid from the resulting (meth)acrylic acid solution, and using the crystallization mother liquor separated from the precipitated crystals of (meth)acrylic acid as a starting material for making a (meth)acrylic acid ester.

7. A process according to claim 6, wherein the second component is an alcohol which does not form a solid solution with (meth)acrylic acid at the time of the crystallization.

8. A process according to claim 7, wherein said alcohol is selected from the group consisting of methanol, ethanol, propanol, and butanol.

9. A process according to claim 8, wherein the second component is methanol.

10. A process according to claim 6, wherein the concentration of the second component is 3–30% by weight.

\* \* \* \* \*